United States Patent [19]

Traber et al.

[11] Patent Number: 4,956,361
[45] Date of Patent: Sep. 11, 1990

[54] NEW COMBINATION PRODUCTS HAVING AN ANTIDEPRESSANT ACTION

[75] Inventors: Jorg Traber, Lohmar; Harald Horstmann, Wuppertal, both of Fed. Rep. of Germany

[73] Assignee: Troponwerke GmbH & Co. KG, Cologne, Fed. Rep. of Germany

[21] Appl. No.: 370,425

[22] Filed: Jun. 23, 1989

Related U.S. Application Data

[63] Continuation-in-part of Ser. No. 197,066, May 19, 1988, abandoned.

[30] Foreign Application Priority Data

Jun. 2, 1987 [DE] Fed. Rep. of Germany ....... 3718398

[51] Int. Cl.$^5$ ............... A61K 31/55; A61K 31/135; A61K 31/435
[52] U.S. Cl. ................... 514/217; 514/277; 514/656
[58] Field of Search .................. 514/217, 277, 656

*Primary Examiner*—Stanley J. Friedman
*Attorney, Agent, or Firm*—Sprung Horn Kramer & Woods

[57] ABSTRACT

The invention relates to combination products with a synergistic action and antidepressant activity, containing substances having antidepressant activity and compounds having antagonistic activity and belonging to the class of dihydropyridines, and to the use of the dihydropyridines in antidepressants.

24 Claims, No Drawings

NEW COMBINATION PRODUCTS HAVING AN ANTIDEPRESSANT ACTION

CONTINUING DATA

This is a continuation-in-part of Ser. No. 197,066, filed May 19, 1988, now abandoned.

The invention relates to combination products with a synergistic action and antidepressant activity, containing substances having antidepressant activity and compounds having antagonistic activity and belonging to the class of dihydropyridines, and to the use of the dihydropyridines in antidepressants.

A large number of substances having antidepressant activity is known from the state of the art, such as, for example, dibenzocycloheptenes and related classes of tricyclic antidepressant structures (compare, for example, U.S. Pat. Nos. 3,438,981, 3,420,851 and 3,534,041, Belgian Pat. No. 61591, J. Org. Chem. 27, 4134 (1962), US Pat. No. 3,505,321 and British Pat. No. 858,187.and 858,188). Compounds from the substance classes of tetracyclic antidepressants, of the monoamine oxidase (MAO) inhibitors, of the basic oxime ethers and others are also used medically as antidepressants (compare oxaprotiline, mianserin, tranylcypromine, pargyline, zimelidine, fluvoxamine and trazodone).

The dihydropyridines having a calcium-antagonistic action are likewise substantially known (compare British Pat. No. 1,173,862 and 1,358,951, and U.S. Pat. No. 4,256,749 and 4,264,611). A number of pharmacological actions have already been described for these dihydropyridines, such as, for example, coronary action, action on blood pressure, diuretic action or antiischaemic action in the cerebral region. A direct antidepressant action or a potentiating action thereon has not hitherto been disclosed for dihydropyridines.

There are indications in the literature that some calcium antagonists such as, for example, verapamil, can be used for the treatment of manic patients (compare Dubovsky SL et al. (1982): Effectiveness of verapamil in the treatment of a manic patient, Am. J. Psychiatry 139; 502–504). Cerebral and neurological actions of dihydropyridines, nimodipine and nicardipine have already been described (compare F. Hoffmeister et al. (1982) ArzneiForsch. 44: 347–360). Nicardipine has also been tested for use as a substance having antimanic activity (compare N. Renwart et al., Prog. Neuro-Psychopharmacol.-Biol. Psychiat. 1986, Vol. 10; 717–722). There emerged from this some differences in the action of dihydropyridines among other calcium antagonists such as verapamil or diltiazem. It emerged as the result of these investigations that calcium antagonists are unsuitable as antimanic active compounds.

Undesired side effects may occur with a number of substances having antidepressant activity which have hitherto been disclosed, especially when these active compounds are administered in high dosages. In addition, difficulties with pharmaceutical formulation often occur when active compounds in relatively high dosage have to be converted into administration forms which ought to be taken by the patients without effort, for example smaller tablets are preferred for oral administration. In general, it is desirable from the medical standpoint for the dosage of active compound to be kept as small as possible. Another disadvantage of some known antidepressants is the relatively late onset of action, which is often not observed in a satisfactory manner until some days after the first administration. A potentiation of the action with a simultaneous reduction in the amount of active compound makes it possible to achieve an earlier onset of the desired effect.

The object of the present invention is to make available antidepressant agents having a low or reduced content of active compound and thus a diminished risk of side effects. This object can be achieved by the combination according to the invention of the antidepressant active compounds with certain dihydropyridines having a calcium-antagonistic action.

The invention relates to the use of dihydropyridines of the general formula (I)

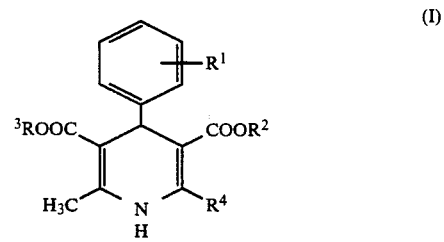

in which $R^1$ represents one or two identical or different substituents from the group comprising nitro, halogen, trifluoromethyl or $OCHF_2$, or represents the radical =N—O—N=, which is fused to the benzene ring.

$R^2$ and $R^3$ are identical or different and each represents alkyl which has 1 to 12 carbon atoms and is optionally substituted by alkoxy having 1 to 4 C atoms, hydroxyl, halogen or N-methyl-N-benzylamino, and $R^4$ represents cyano or alkyl which has 1 to 4 carbon atoms and is optionally substituted by hydroxyl or halogen, as antidepressants, in particular for potentiating the antidepressant action in combination products with compounds having antidepressant activity.

Particularly important are dihydropyridines from the group comprising nifedipine, niludipine, nisoldipine, nitrendipine, nimodipine, felodipine and nicardipine.

The following compounds are particularly suitable for the potentiation of their antidepressant effect according to the invention: nortriptyline, amitriptyline, imipramine, desipramine, doxepine, citalopram, fluoxetine, fluvoxamine, mianserin, oxaprotiline and maprotiline.

Surprisingly, this superadditive action-potentiating effect is achieved only by use of calcium antagonists belonging to the said dihydropyridine class. Calcium antagonists from other substance classes, such as, for example, verapamil or diltiazem, do not show this potentiating effect.

The experiments which follow demonstrate by way of example the unexpected, superadditive synergistic effect by combination of some exemplary antidepressants with dihydropyridines having calcium-antagonistic activity.

Test method

Male albino mice which have been housed under standard laboratory conditions with free access to feed and water are placed for 6 minutes in a cylinder filled with water. After some time, the mice give up the attempt to escape from the water and subside into immobility. The duration of the immobility during the last 4 minutes is measured. The duration of the immobility for untreated control groups is 2 to 3 minutes. Many antidepressants shorten the duration of the immobility when they are administered to the mouse in a relatively high dose (about 30 mg/kg), whereas this effect is not observed at lower dosage. Surprisingly, however, the immobility period is shortened after administration of the combination with dihydropyridines according to the invention even after a low dosage (description of the method: R. B. Porsolt et al., Biochem. Pharmacol. 34, 3837 (1977)).

Table 1 which follows shows the results after single and after combined administration of the various relevant active compounds.

TABLE 1

Action on the duration of the immobility of mice during the last 4 minutes of the 6-minute water test on separate and on simultaneous administration of nifedipine and various antidepressants. (In each case, means of 10 animals per experiment).

| Type of treatment (active compound) | *Dose (mg/kg) | duration of the immobility (s) mean (± S.E.M.) |
|---|---|---|
| Control | — | 157.3 (9.1) |
| Imipramine | 10 | 174.6 (12.2) |
| Mianserin | 10 | 184.4 (14.0) |
| Citalopram | 10 | 192.6 (16.3) |
| Control | — | 157.3 (9.1) |
| Nifedipine + imipramine | 20 + 10 | 24.2 (5.1) |
| Nifedipine + mianserin | 20 + 20 | 20.6 (3.2) |
| Nifedipine + citalopram | 20 + 10 | 23.3 (7.4) |
| Control | — | 155.2 (12.4) |
| (+)Oxaprotiline | 5 | 111.0 (6.7) |
| Nifedipine + (+)oxaprotiline | 20 + 5 | 21.1 (3.5) |
| Control | — | 163.4 (13.3) |
| Nifedipine | 20 | 101.3 (10.4) |
| (−)Oxaprotiline | 30 | 130.7 (12.1) |
| Nifedipine + (−)oxaprotiline | 20 + 20 | 67.8 (6.8) |

*The antidepressants are administered intraperitoneally and the dihydropyridines orally; in each case 30 minutes before the start of the test.

Table 2 shows the antidepressant action of some exemplary dihydropyridines compared with the absence of an action with calcium antagonists belonging to other substance classes, such as, for example, verapamil or diltiazem.

TABLE 2

| Type of treatment (active compound) | Dose (mg/kg) | Duration of the immobility (s) mean (± S.E.M.) |
|---|---|---|
| Dihydropyridines | | |
| Control | — | 151.6 (9.4) |
| Nifedipine | 0.1 | 147.0 (9.5) |
| | 1.0 | 79.1 (10.2) |
| | 10.0 | 42.7 (4.4) |
| Control | — | 126.6 (9.9) |
| Nitrendipine | 0.1 | 99.2 (11.2) |
| | 1.0 | 62.4 (4.6) |
| | 10.0 | 44.0 (4.1) |
| Phenylalkylamines | | |
| Control | — | 165.5 (8.3) |
| Verapamil | 0.1 | 142.1 (9.7) |
| | 1.0 | 180.5 (7.0) |
| | 10.0 | 163.5 (12.3) |
| Benzothiazepines | | |
| Control | — | 148.1 (8.3) |
| Diltiazem | 0.1 | 135.3 (12.6) |
| | 1.0 | 142.1 (10.0) |
| | 10.0 | 137.9 (11.5) |

Particularly suitable combination products according to the invention are those whose daily dose for the antidepressant active compound is 10 to 200 mg, in particular 20 to 100 mg, and for the dihydropyridines having calcium-antagonistic activity is 5 to 100 mg, in particular 10 to 50 mg. These amounts of active compound can be distributed as a single dosage or over several dosages per day.

The combination products according to the invention can be used in customary pharmaceutical formulations such as tablets, capsules, coated tablets, granules, syrups, emulsions, suspensions and solutions, using inert, pharmaceutically suitable vehicles and solvents. The therapeutically active compounds should in each case be present in a concentration of about 1 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents, and, for example when using water as a diluent, organic solvents can optionally be used as auxiliary solvents.

Examples of auxiliaries which may be mentioned are: water, non-toxic organic solvents such as paraffins (for example petroleum fractions), vegetable oils (for example groundnut/sesame oil), alcohols (for example ethyl alcohol and glycerol), glycols (for example propylene glycol and polyethylene glycol), solid vehicles such as, for example, natural rock powders (for example kaolins, aluminas, talc and chalk), synthetic rock powders (for example highly disperse silica and silicates), sugars (for example sucrose, lactose and glucose), emulsifiers (for example polyoxyethylene fatty acid esters), polyoxyethylene fatty alcohol ethers (for example lignin, sulphite waste liquors, methylcellulose, starch and polyvinylpyrrolidone) and lubricants (for example magnesium stearate, talc, stearic acid and sodium sulphate).

Administration is effected in the customary manner, preferably orally or parenterally, in particular perlingually or intravenously. In the case of oral administration, the tablets can, of course, also contain in addition to the vehicles mentioned, additives such as sodium citrate, calcium carbonate and dicalcium phosphate, together with various additional substances, such as starch, preferably potato starch, gelatine and/or the like. Furthermore, lubricants such as magnesium stearate, sodium lauryl sulphate and talc can also be used when making tablets. In the case of aqueous suspensions and/ or elixirs which are intended for oral use, the active compounds can be mixed with various flavor improving agents or colorants in addition to the abovementioned auxiliaries.

In the case of parenteral administration, solutions of the active compounds, employing suitable liquid vehicles, can be used.

In general, it has proved advantageous, in the case of intravenous administration, to administer amounts of about 0.001 to 0.5 mg/kg, preferably about 0.01 to 0.2 mg/kg, of body weight to achieve effective results, and in the case of oral administration, the dosage is about 0.05 to 5 mg/kg, preferably 0.1 to 3 mg/kg, of body weight.

Nevertheless, it can at times be necessary to deviate from the amounts mentioned, and in particular to do so as a function of the body weight of the experimental animal or of the nature of the administration method, but also because of the species of animal and its individual behavior towards the medicament, or the nature of the formulation of the medicament and the time or interval over which the administration takes place.

Thus, it can suffice in some cases to manage with less than the abovementioned minimum amount, while in other cases the upper limit mentioned must be exceeded. Where relatively large amounts are administered, it can be advisable to divide these into several individual administrations over the course of the day. The same dosage range is envisaged for administration in human medicine. In this connection, the above statements similarly apply.

It will be appreciated that the instant specification and claims are set forth by way of illustration and not limitation, and that various modifications and changes may be made without departing from the spirit and scope of the present invention.

What is claimed is:

1. A method of potentiating antidepressant activity in a patient which comprises administering to such patient an antidepressant composition comprising 5 to 100 parts by weight of nifedipine and 10 to 200 parts by weight of an antidepressant selected from the group consisting of imipramine, oxaprotiline, and desimipramine.

2. The method according to claim 1 wherein the antidepressant as present in the antidepressant composition in the amount 20 to 100 parts by weight and nifedipine is present in the antidepressant composition in the amount 10 to 50 parts by weight.

3. An antidepressant composition comprising 5 to 100 parts by weight of nifedipine and 10 to 200 parts by weight of an antidepressant selected from the group consisting of imipramine, oxaprotiline, and desimipramine.

4. The composition according to claim 3 wherein the antidepressant is present in the amount 20 to 100 parts by weight and nifedipine is present in the amount 10 to 50 parts by weight.

5. A method of potentiating antidepressant activity in a patient which comprises administering to such patient an antidepressant composition comprising 5 to 100 parts by weight of nifedipine and 10 to 200 parts by weight of oxaprotiline.

6. The method according to claim 5 wherein the composition contains 20 to 100 parts by weight of oxaprotiline and 10 to 50 parts by weight of nifedipine.

7. An antidepressant composition comprising 5 to 100 parts by weight of nifedipine and 10 to 200 parts by weight of oxaprotiline.

8. The composition according to claim 7 comprising 10 to 50 parts by weight of nifedipine and 20 to 100 parts by weight of oxaprotiline.

9. A method of potentiating antidepressant activity in a patient which comprises administering to such patient an antidepressant composition comprising 5 to 100 parts by weight of nifedipine and 10 to 200 parts by weight of imipramine.

10. The method according to claim 9 wherein the composition contains 20 to 100 parts by weight of imipramine and 10 to 50 parts by weight of nifedipine.

11. An antidepressant composition comprising 5 to 100 parts by weight of nifedipine and 10 to 200 parts by weight of imipramine.

12. The composition according to claim 11 comprising 10 to 50 parts by weight of nifedipine and 20 to 100 parts by weight of imipramine.

13. A method of potentiating antidepressant activity in a patient which comprises administering to such patient an antidepressant composition comprising 5 to 100 parts by weight of nimodipine and 10 to 200 parts by weight of maprotiline.

14. The method according to claim 13 wherein the composition contains 20 to 100 parts by weight of maprotiline and 10 to 50 parts by weight of nimodipine.

15. An antidepressant composition comprising 5 to 100 parts by weight of nimodipine and 10 to 200 parts by weight of maprotiline.

16. The composition according to claim 15 comprising 10 to 50 parts by weight of nimodipine and 20 to 100 parts by weight of maprotiline.

17. A method of potentiating antidepressant activity in a patient which comprises administering to such patient an antidepressant composition comprising 5 to 100 parts by weight of nimodipine and 10 to 200 parts by weight of an antidepressant selected from the group consisting of nortriptyline, amitriptyline, imipramine, desipramine, citalopram, fluoxetine, fluvoxamine, mianserin, oxaprotiline, and maprotiline.

18. The method according to claim 17 wherein the antidepressant is present in the antidepressant composition in the amount 20 to 100 parts by weight and nimodipine is present in the antidepressant composition in the amount 10 to 50 parts by weight.

19. An antidepressant composition comprising 5 to 100 parts by weight of nimodipine and 10 to 200 parts by weight of an antidepressant selected from the group consisting of nortriptyline, amitriptyline, imipramine, desipramine, citalopram, fluoxetine, fluvoxamine, mianserin, oxaprotiline, and maprotiline.

20. The composition according to claim 19 wherein the antidepressant is present in the amount 20 to 100 parts by weight and nimodipine is present in the amount 10 to 50 parts by weight.

21. A method of potentiating antidepressant activity in a patient which comprises administering to such patient an antidepressant composition comprising 5 to 100 parts by weight of nimodipine and 10 to 200 parts by weight of fluoxetine.

22. The method according to claim 21 wherein the composition contains 20 to 100 parts by weight of fluoxetine and 10 to 50 parts by weight of nimodipine.

23. An antidepressant composition comprising 5 to 100 parts by weight of nimodipine and 10 to 200 parts by weight of fluoxetine.

24. The composition according to claim 23 comprising 10 to 50 parts by weight of nimodipine and 20 to 100 parts by weight of fluoxetine.

* * * * *